(12) United States Patent
Jafari et al.

(10) Patent No.: US 8,449,687 B2
(45) Date of Patent: May 28, 2013

(54) WASH RING ASSEMBLY AND METHOD OF USE

(75) Inventors: Nasser Jafari, American Canyon, CA (US); Lawrence Blecka, Walnut Creek, CA (US); Chris Tsai, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 101 days.

(21) Appl. No.: 13/372,300

(22) Filed: Feb. 13, 2012

(65) Prior Publication Data

US 2012/0138099 A1    Jun. 7, 2012

Related U.S. Application Data

(62) Division of application No. 12/118,367, filed on May 9, 2008, now Pat. No. 8,136,539.

(60) Provisional application No. 60/928,803, filed on May 11, 2007.

(51) Int. Cl.
*B08B 5/04*    (2006.01)
*B08B 3/04*    (2006.01)

(52) U.S. Cl.
USPC .............. 134/22.11; 134/18; 134/21; 134/42; 134/137; 134/902

(58) Field of Classification Search
USPC .............. 134/18, 21, 22.11, 42, 44, 52, 56 R, 134/104.1, 104.2, 137, 140, 147, 148, 151, 134/152, 157, 902
See application file for complete search history.

(56) References Cited

U.S. PATENT DOCUMENTS

| | | |
|---|---|---|
| 4,217,780 A | 8/1980 | O'Connell et al. |
| 4,311,484 A | 1/1982 | Fosslien |
| 4,318,885 A | 3/1982 | Suzuki et al. |
| 4,516,437 A | 5/1985 | Pedroso et al. |
| 4,817,443 A | 4/1989 | Champseix et al. |
| 4,820,497 A | 4/1989 | Howell |
| 4,989,623 A | 2/1991 | Hoffman et al. |
| 5,066,336 A | 11/1991 | Hoffman et al. |
| 5,186,194 A | 2/1993 | Kitajima |
| 5,279,794 A * | 1/1994 | Sasao ............................. 422/510 |
| 5,318,359 A | 6/1994 | Wakatake |
| 5,408,891 A | 4/1995 | Barber et al. |
| 5,474,744 A | 12/1995 | Lerch |

(Continued)

OTHER PUBLICATIONS

ISA/US, PCT International Search Report and Written Opinion dated Jul. 28, 2008 for PCT/US2008/005805.

*Primary Examiner* — Michael Barr
*Assistant Examiner* — Benjamin L Osterhout
(74) *Attorney, Agent, or Firm* — Jones Day

(57) ABSTRACT

Devices, including a wash ring assembly, and methods are provided for the removal of excess fluid or solids from the exterior or interior of a probe used to transfer fluids, for instance, in an automated assay device. Typically, a probe is used to aspirate and dispense a sample fluid material such as whole blood or a reagent. The devices and methods provided herein are useful for removing excess fluid from the exterior or interior of the probe so as to prevent dripping and cross-contamination between samples or reagents. It is also contemplated that, utilizing the devices and methods provided herein, washing and/or drying can be performed simultaneously as the probe is in motion, aspirating a sample and/or dispensing a sample.

7 Claims, 8 Drawing Sheets

U.S. PATENT DOCUMENTS

| | | | |
|---|---|---|---|
| 5,511,568 A * | 4/1996 | Bowman et al. | 134/102.2 |
| 5,569,861 A | 10/1996 | Le Comte et al. | |
| 5,592,959 A | 1/1997 | Nagai | |
| 5,603,342 A | 2/1997 | Shambaugh | |
| 5,803,987 A * | 9/1998 | DeWitt et al. | 134/25.4 |
| 5,827,744 A * | 10/1998 | Fose et al. | 436/49 |
| 5,882,594 A | 3/1999 | Kawaguchi et al. | |
| 6,003,531 A | 12/1999 | Kimura et al. | |
| 6,066,298 A | 5/2000 | Fukunaga | |
| 6,190,614 B1 | 2/2001 | Fukunaga | |
| 6,422,248 B1 | 7/2002 | Furst et al. | |
| 6,526,812 B2 | 3/2003 | Martin et al. | |
| 6,575,181 B1 | 6/2003 | Wimmer | |
| 6,955,180 B2 * | 10/2005 | Kocherlakota et al. | 134/169 C |
| 2002/0185161 A1 | 12/2002 | Furst et al. | |
| 2005/0123445 A1 | 6/2005 | Blecka et al. | |
| 2006/0179946 A1 | 8/2006 | Wilson | |

\* cited by examiner

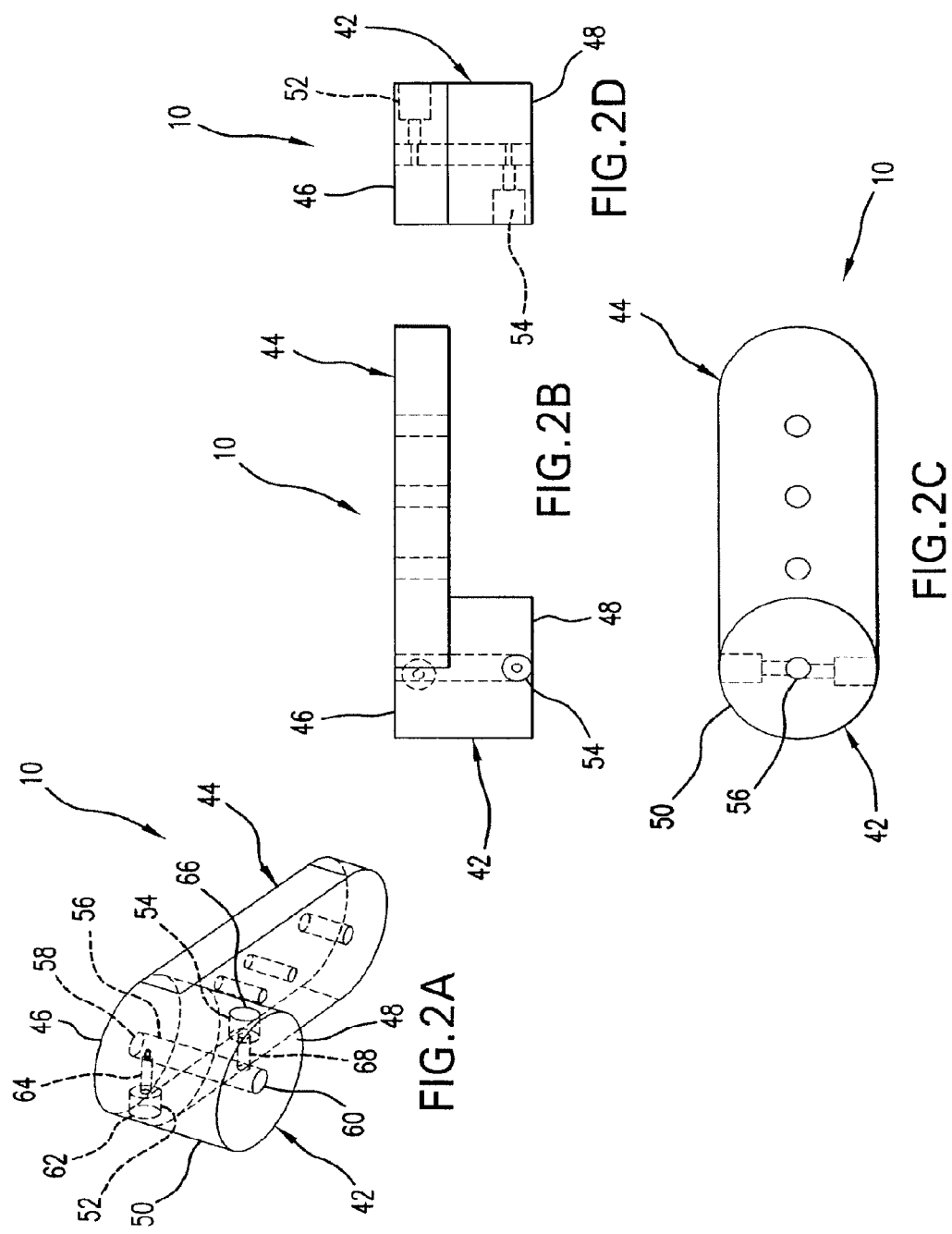

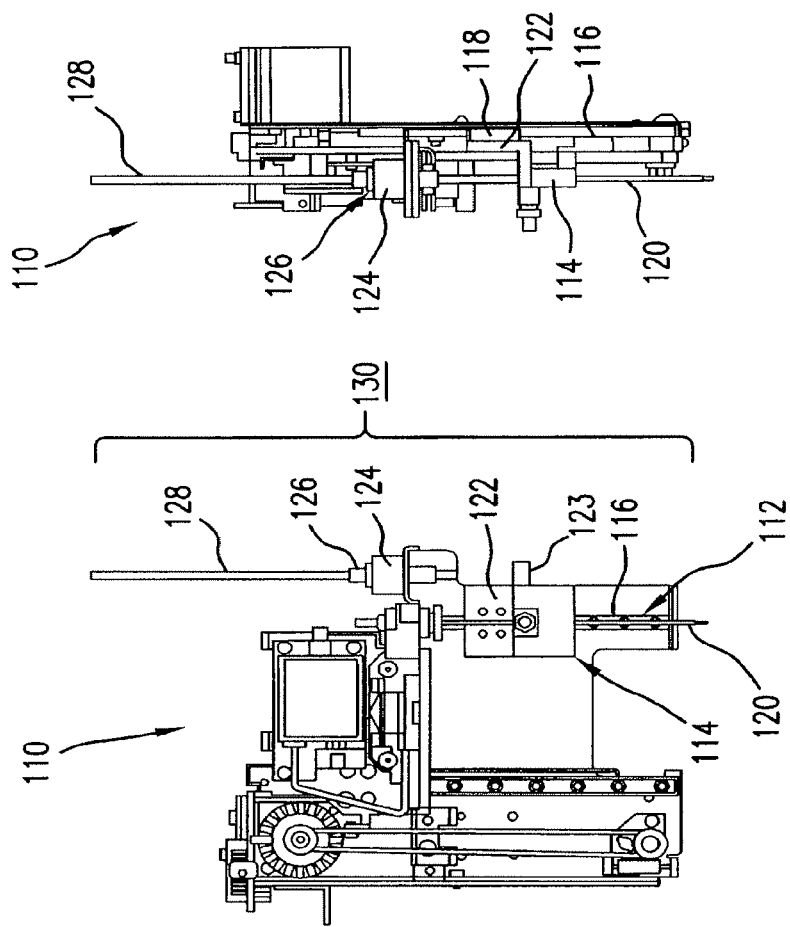
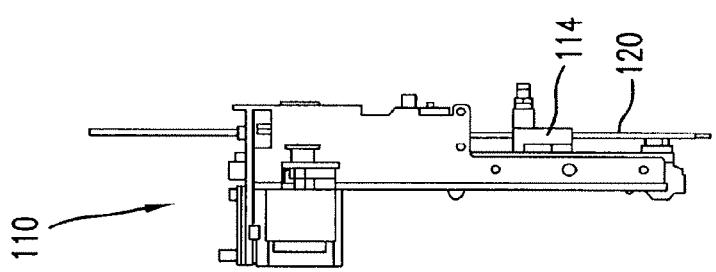

WASH RING ASSEMBLY AND METHOD OF USE

CROSS-REFERENCE TO RELATED APPLICATIONS

This application is a divisional of U.S. patent application Ser. No. 12/118,367, filed May 9, 2008, which claims the benefit of U.S. Provisional Application No. 60/928,803, filed May 11, 2007, the contents of which are incorporated by reference in their entireties.

FIELD

This application generally relates to devices and methods for washing a probe that transfers fluids, for instance, in an automated assay device. For example, this application provides a wash ring assembly useful for washing and drying the exterior and interior of a probe.

BACKGROUND

Automated assay techniques are crucial for disease analysis, bio-research and drug development in the medical and pharmaceutical industries. With incorporation of high-throughput steps, automated assay techniques can provide more results in a given amount of time than manual assay techniques. Automated assay techniques can reduce the risks of exposing personnel to potentially hazardous biological materials or chemicals. Modern automated assay devices can transport materials, such as biological samples, assay reagents, buffers, wash solutions, and the like, between a number of stations located in the devices. For instance, in a typical simple automated device a probe may aspirate sample from a sample vial located at a first station in the device, travel to and dispense the sample in a reaction container located at a second station in the device, travel to a wash station at a third location to aspirate and dispense a wash solution, and then return to the first station to aspirate sample from another sample vial. Three, four or more aspiration and dispensing stations can be found in commercially available automated devices. An exemplary automated device in described in U.S. Pat. Pub. No. 20050123445, published Jun. 9, 2005.

Typically, the probe should be thoroughly washed between aspirations and dispensations of different samples to avoid carryover or contamination. This is in part because carryover can adversely affect (usually add to) the volume of the dispensed sample. For instance, inaccurate results can occur where the volume of carryover sample is significant when added to the volume of dispensed sample. In addition, assay errors can occur due to cross-contamination between different samples being tested. While washing a probe is essential to obtaining accurate results in an automated assay device, it is also advantageous to reduce the time it takes to handle consecutive samples. Thus, it is desirable to reduce the time it takes to automatically wash the probe such as by reducing the distance the probe travels during the wash cycle.

SUMMARY

In one aspect, a wash ring is provided for removing excess fluid or solids from the exterior or interior of a probe after the probe has been immersed into the contents of a container. The container may hold a sample fluid material such as whole blood or a reagent.

An exemplary wash ring contains an outer surface and an inner surface, wherein the inner surface forms a bore that is open to atmosphere at both ends. The bore can be adapted to receive a probe, such that when the probe is present in the bore, a capillary is formed between the probe and the inner surface. The exemplary wash ring can be equipped with inlet opening in an upper portion of the bore through which, for example, wash fluid can be added into the bore. The exemplary wash also has an outlet opening in a lower portion or the bore through which, for example, fluid can be expelled from the bore. In certain embodiments, the side in which the inlet opening into the bore is located opposes the side of bore in the outlet opening is located. In some embodiments, the outlet opening in the bore is larger than the inlet opening in the bore.

In one aspect, a wash ring assembly is provided, wherein the wash ring assembly comprises a frame mountable on a robotic probe assembly, such as that described, for instance, in U.S. Pat. Pub. No. 20050123445, published Jun. 9, 2005, which is hereby incorporated by reference in its entirety for all purposes, a wash ring, and a coupling means, wherein the wash ring is coupled to the frame by the coupling means, wherein the coupling means is capable of moving the wash ring toward and away from the frame in parallel to a longitudinal axis of the probe when the probe is present in the bore. In certain embodiments, the coupling means comprises a bearing, a lead screw and a motor.

In some embodiments, the wash ring assembly provided can further include a bearing assembly, useful, for example, for ensuring that the motion of the wash ring remains on a path parallel to the longitudinal axis of the probe as it is propelled by the coupling means. For instance, the bearing assembly can comprise a bearing and a sled, wherein the bearing is coupled to the robotic probe assembly and the sled is coupled to the wash ring.

In one aspect, a robotic aspiration and dispensing system is provided. The robotic aspiration and dispensing system can comprise a wash ring assembly, as described herein, which is mounted on a robotic probe assembly. The robotic aspiration and dispensing system can further comprise a pumping means for pumping fluid through the inlet port into the bore of the wash ring component of the wash ring assembly and a suction means for removing fluid from the bore of the wash ring through the outlet port. Typically, the probe extends through the bore of the wash ring, and the wash ring and probe move together as the robotic aspiration and dispensing system moves the probe to desired locations to aspirate and/or dispense fluids. This affords the ability washing or drying the probe during any stage before, during or after the probe is used to handle a sample.

An exemplary process of using the wash ring assembly is described below. Prior to aspirating a sample from a container, a robotic probe assembly including a probe and an attached wash ring are brought into a position above the container. As the tip of the probe is lowered toward the container, the wash ring is positioned over an upper portion of the probe away from the tip of the probe. The probe is lowered by the robotic probe assembly and immersed in the sample, a portion of which can be aspirated into the probe. The wash ring can be moved down along the vertical axis of the probe toward the probe tip so as to be in position to wash the probe exterior as it is withdrawn from the sample container. This occurs while wash fluid enters the bore of the wash ring through the inlet, passes through the bore, and/or leaves by way of the outlet in the bore of the wash ring. The probe is then positioned over a dispensing container to dispense the sample. The wash ring can wash the probe, for example, following sample aspiration, as the probe moves prior to dispensing the sample and/or as the probe, after dispensing the sample, is moving to another position, for example, over a second container with a sample to be aspirated.

If desired, more than one cycle of exterior probe washing can take place while the robotic probe assembly is moved from its respective aspiration and dispense stations. Alternately or additionally, the wash ring devices and methods can be used to remove fluids from the interior and exterior of probes immersed in any substance, including reagents, buffers and sample treatment formulations.

Other improvements and advantages will be apparent to those skilled in the art from the Figures, description and claims set forth below.

DESCRIPTION OF THE FIGURES

FIG. 2A is a perspective view of an exemplary wash ring for use, for instance, in the exemplary robotic aspiration and dispensing system of FIG. 1.

FIG. 2B is a front view of the exemplary wash ring of FIG. 2A.

FIG. 2C is a top view of the exemplary wash ring of FIG. 2A.

FIG. 2D is a side view of the exemplary wash ring of FIG. 2A.

FIG. 4A is a front view of another exemplary robotic aspiration and dispensing system.

FIG. 4B is a left side view of the exemplary robotic aspiration and dispensing system of FIG. 4A.

FIG. 4C is a right side view of the exemplary robotic aspiration and dispensing system of FIG. 4A.

DETAILED DESCRIPTION

Provided herein are devices and methods for washing or removing fluid or solids from the exterior and/or interior of a probe in an automated aspirating and dispensing device. The devices and methods provided herein can be used, for instance, to avoid dripping from probes and cross-contamination between samples and/or reagents in an automated aspirating and dispensing device. In certain embodiments, probe washing can be performed prior to, simultaneously, or after aspirating and/or dispensing materials with the probe.

Figure 1:
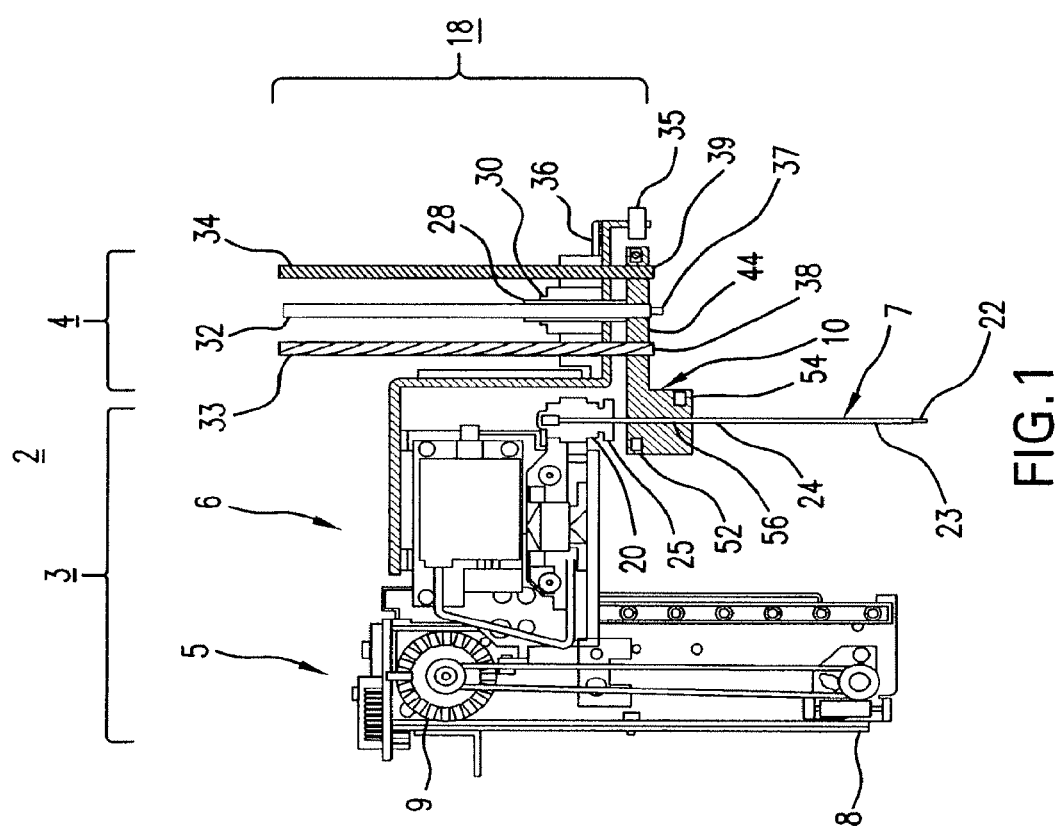
FIG. 1 is a front view of an exemplary robotic aspiration and dispensing system.

FIG. 1 is a front view of an exemplary robotic aspiration and dispensing system 2 which has a robotic probe assembly 3 and a wash ring assembly 4.

The robotic probe assembly 3 has a vertical column and motor assembly 5, a probe mount assembly 6, and a probe 7 which is mounted to the probe mount assembly 6. The vertical column and motor assembly 5 has a motor 8 which employs a belt and gear system 9 to move the probe mount assembly 6 and also the wash ring assembly 4 up and down in vertical direction.

It will be appreciated that the robotic probe assembly 3 including probe 7 together with wash ring assembly 4 can also move in horizontal directions using components not shown in FIG. 1. For instance, horizontal motion of the robotic probe assembly 3 together with wash ring assembly 4 along a gantry and rail bearing can be driven by motors as described in FIG. 22 and accompanying description of U.S. Pat. Pub No. 20050123445, published Jun. 9, 2005, incorporated herein by reference for all purposes. Hence, the wash ring 10 can, for example, be moved relative to the probe 7 in a vertical direction while the probe 7 is moved relative to the ground in a vertical direction, horizontal direction or a combination of horizontal directions or vertical and horizontal directions.

In an exemplary probe mount assembly 6, the probe 7 is threaded into a probe mount 20, which is located on the underside of the probe mount assembly 6, with a small o-ring providing a seal. The probe mount assembly 6 (along with the probe 7 and the wash ring assembly 4) is able to travel vertically under the control of the vertical column and motor assembly 5. In certain embodiments, the robotic aspiration and dispensing system 2, or any other robotic aspiration and dispensing system described herein, is mounted to an automated assay instrument such as the automated assay instrument described in U.S. Patent Publication No. 20050123445, published Jun. 9, 2005, which is hereby incorporated by reference as if fully set forth herein.

In the exemplary embodiment, the wash ring assembly 4 has a wash ring 10 and a wash ring control and guiding assembly 18. The wash ring 10 is able to move vertically up and down along the long axis of the probe 7 under control of the wash ring control and guiding assembly 18. Alternatively, the wash ring is attached to an air cylinder for vertical movement, for example, as discussed below.

The wash ring control and guiding assembly 18 comprises a lead screw 28, a motor 30, a bearing 32, a first guide shaft 33, a second guide shaft 34, a sensor 35, and a bracket 36. The lead screw 28 and the motor 30 are fixed on the bracket 36 which can be mounted to the probe mount assembly 6 so that bracket 36 (and also the whole wash ring assembly 4) moves with probe mount assembly 6. Therefore, the position and movement of the wash ring 10 are controlled by both the wash ring control and guiding assembly 18 and the probe mount assembly 6. In certain embodiments, a wash ring control and guiding assembly comprises a lead screw and a single guide shaft.

For example, when the probe mount assembly 6 moves down, both the probe 7 and the wash ring 10 moves down along with the probe mount assembly 6. However, the wash ring 10 can also be moved toward the probe tip 22 and back to the probe head 25 by controlling of the wash ring control and guiding assembly 18. When the wash ring 10 is moved toward the position farthest away from the probe tip 22, the probe 7 can be immersed deeply into fluids such as whole blood or any other fluid.

The lead screw 28, the motor 30, and the bearing 32 are used to move and guide the wash ring 10 vertically up and down to a desired position. The bearing 32 is engaged with the lead screw 28 which is controlled by the motor 30. The motor 30 used here can be any stepping motor or linear motor that can be synchronized with the motor 8 of the vertical column and motor assembly 5. Alternatively, an air cylinder attached to the probe mount assembly 6 and the wash ring 10 can be utilized.

One end of the bearing 32 is fixed to through bore 37 on a wash ring support 44 of the wash ring 10. When the motor 30 drives, the lead screw 28 follows and screws the bearing 32 up or down depending on the direction of driving on the lead screw 28. The wash ring 10 is then moved up or down by virtue of a pull or push from the bearing 32. When the wash ring 10 moves, the probe mount assembly 6 (as well as the probe 7) can be either in a steady position or in motion relative to the ground. Therefore, the wash ring 10 can be moved relative to the probe 7 in vertical direction while the probe 7 (and also the probe mount assembly 6) can be moved relative to the ground in a vertical direction.

The lower end of the first guide shaft 33 is connected and fixed to the wash ring support 44 of the wash ring 10 at a bore 38 and the lower end of the second guide shaft 34 is connected and fixed to the wash ring support 44 of the wash ring 10 at a bore 39. The first and second guide shafts 33, 34 are able to travel freely up and down, each through a hole in the bracket 36, together with the wash ring 10 in order to guide and stabilize movement of the wash ring 10. One of the purposes of using the guide shafts 33, 34 is to maintain the proper position of the wash ring, particularly the bore of the wash ring, with respect to the probe, during movements of the probe assembly. Dampening the effects of vibration can be important, since vibration may cause the probe 7 and the wash ring 10 to come into contact with one another.

The sensor 35 is placed at the end of the bracket 36 so as to monitor the position of the wash ring 10 and to feedback the status to a controller to stop or slow down the motor 30 as needed.

In the exemplary embodiment, the probe 7 has a probe tip 22, a probe body 23, a probe base 24, and a probe head 25. The probe tip 22 has a thinner interior diameter than that of the probe body 23 and the probe base 24 so as to increase the velocity of fluid dispensed through the probe tip 22. In this way, the probe dispenses fluid with greater accuracy. The probe head 25 is threaded into the probe mount 20 of the probe mount assembly 6. The probe head 25 can be connected to a syringe pump (not shown) or tubing filled with buffer fluid. Depending on the application, the probe 7 described above can be a reagent probe, a sample probe, an aspiration probe or any combination thereof.

In certain embodiments, the probe and its operation are as described in Section 5.3 of U.S. Patent Publication No. 20050123445, published Jun. 9, 2005, which is hereby incorporated by reference as if fully set forth herein. In some embodiments, the probe mount assembly 6 including probe 7 comprises a sample liquid level sensing and blockage detection system as are described in Section 5.3 of U.S. Patent Publication No. 20050123445, published Jun. 9, 2005, which is hereby incorporated by reference as if fully set forth herein.

FIG. 2A is a perspective view of an exemplary wash ring 10 for use, for instance, in the exemplary robotic aspiration and dispensing system 2 of FIG. 1. FIG. 2B is a front view of the exemplary wash ring 10 of FIG. 2A. FIG. 2C is a top view of the exemplary wash ring 10 of FIG. 2A. FIG. 2D is a side view of the exemplary wash ring 10 of FIG. 2A. The wash ring 10 has a cylindrical wash ring body 42 and a wash ring support 44. The cylindrical wash ring body 42 has a top surface 46, a bottom surface 48, a cylindrical side wall 50, an inlet 52, an outlet 54, and a bore 56. The bore 56 has an upper port 58 opened at the top surface 46 and a lower port 60 opened at the bottom surface 48.

In the exemplary embodiment, the inlet 52 (also called a liquid port) is located at the upper portion of the wash ring body 42 with a larger open end 62 to be hooked up to a tube (not shown) for wash fluid supply. A smaller end 64 of the inlet 52 is opened to the upper portion of the wash ring bore 56. The wash fluid can be pumped into the wash ring bore 56 through the inlet 52 from the larger open end 62 of the inlet 52 to the smaller end 64 of the inlet 52.

The outlet 54 (preferably a vacuum port) is located at the lower portion of the wash ring body 42 with a larger open end 66 to be hooked up to a tube (not shown) for drainage of waste liquid or substance. A smaller end 68 of the outlet 54 is opened to the lower portion of the wash ring bore 56. The waste fluid or substance in the wash ring bore 56 can be sucked out through the outlet 54 from the smaller end 68 of the outlet 54 to the larger open end 66 of the outlet 54.

The inner diameter of the smaller end 68 of the outlet 54 is larger than the inner diameter of the smaller end 64 of the inlet 52. In some embodiments, the inner diameter of the smaller end 64 is about 0.25× to about 0.75× the inner diameter of the smaller end 68. In some embodiments, the inner diameter of the smaller end 64 is about 0.25× to about 0.5× the inner diameter of the smaller end 68. In certain embodiments, the inner diameter of the smaller end 64 is about 0.5× the inner diameter of the smaller end 68. The inner diameter of the smaller end 68 of the outlet 54 can, for example, be about 0.02 to about 0.8 inches, about 0.025 inches to about 0.5 inches, or about 0.03 inches to about 0.15 inches. The inner diameter of the smaller end 64 of the inlet 52 can, for example, be about 0.01 to about 0.4 inches, about 0.0125 inches to about 0.25 inches, or about 0.015 inches to about 0.075 inches. The differences of the inner diameters allow, for instance, the output vacuum flow rate through the outlet 54 to be greater than that of the input fluid flow rate into the inlet 52. Since both the upper port 58 and the lower port 60 of the wash ring bore 56 are open to atmosphere, this flow rate difference is able to prevent the wash fluid from escaping from the wash ring bore 56 so as to prevent any fluid leakage or dripping. Depending on the power of the output vacuum, the output vacuum flow rate can be two times to four times greater than the input fluid flow rate.

In the exemplary embodiment, the larger open end 62 of the inlet 52 and the larger open end 66 of the outlet 54 are located at the opposite sides of the cylindrical side wall 50 so that wash fluid coming from the inlet 52 would be forced to flush not only from up to down but also from one side of the bore 56 to the other side. Without intending to be limited to any particular theory or mechanism, it is believed that having the inlet and outlet opening in opposing sides of the bore 56 can lead to a more thorough wash. In various embodiments, the inlet 52 and the outlet 54 can be set up from about 90° to about 180° apart relative to the long axis of the wash ring bore 56.

In the exemplary embodiment, the inner diameter of the bore 56 is sized to receive a probe 7. The space between the interior surface of the bore 56 and the exterior surface of the probe 7 forms a passage for wash fluid to rinse or wash the probe 7. In certain embodiments, the space between the interior surface of the bore 56 and the exterior surface of the probe 7 is in the range of about 0.008 inches to about 0.12 inches, about 0.01 inches to 0.12 inches, or about 0.03 inches to 0.08 inches. Without intending to be limited to any particular theory or mechanism, it is believed that this spacing and the use of aqueous fluids, typically used in the devices and methods for washing a probed as described herein, are conducive for maintaining capillary action to draw fluid entering the bore 56 out of the bore by way of the outlet. As such, the device provided herein is capable of both washing and drying the probe.

For example, the inner diameter of the bore 56 is 0.116 inches while the outer diameter of the probe base 24 is about 0.10 inches, and the outer diameter of the probe body 23 is about 0.07 inches. Therefore, capillary action can be formed when either the probe base 24 or the probe body 23 are within the bore 56. This capillary action and the spiral flow of liquid previously described would provide a thoroughly cleaning of the exterior of the probe 7, thereby preventing cross-contamination of samples or reagents.

The interior surface of the bore 56 can be made of, or coated with, a hydrophobic material, such as plastic, silicon, polyethylene, TEFLON, or other materials constructed by particles in nanometer dimension.

In certain embodiments, the inner surface of bore 56 is a smooth surface.

An exemplary probe cleaning method using the wash ring assembly 10 of FIG. 1 is described below. In this exemplary process, the probe mount assembly 6 is in a ready position. The probe 7 is inserted into the wash ring 10 and vertically passed through the bore 56 with the wash ring 10 at its uppermost position relative to the probe 7 as shown in FIG. 1. The probe 7 and the wash ring 10 are then moved to align with the center axis of a sample container (not shown). Then, the probe 7 is lowered and immersed into the contents of sample container to the desired depth. Then, a sample is aspirated into the probe 7. The probe 7 is then raised up from the sample container, repositioned over and lowered into a receiving vessel into which the sample is dispensed. The probe 7 is then raised up. A wash fluid is inserted into the bore 56 through the inlet 52, wherein the exterior of the probe 7 is washed as the wash ring 10, propelled by wash ring control and guiding assembly 18, passes along the probe 7 toward the probe tip 22. When the probe tip 22 is located in the bore 56, the wash fluid in the bore 56, and any aspirating fluid or substance within the probe 7 expelled from the interior of the probe 7 through probe tip 22, are removed from the bore 56 through the outlet 54 so as to clean the interior of the probe 7.

The cleaning of the exterior of the probe 7 therefore may occur when the wash ring 10 is moving relative to the probe tip 22. Thus, the exemplary embodiment is capable of washing while simultaneously aspirating and dispensing of fluids into a vessel. This capability, for instance, minimizes the cleaning cycle time and reduces the overall processing time in an automated assay analysis system.

Figure 3C:
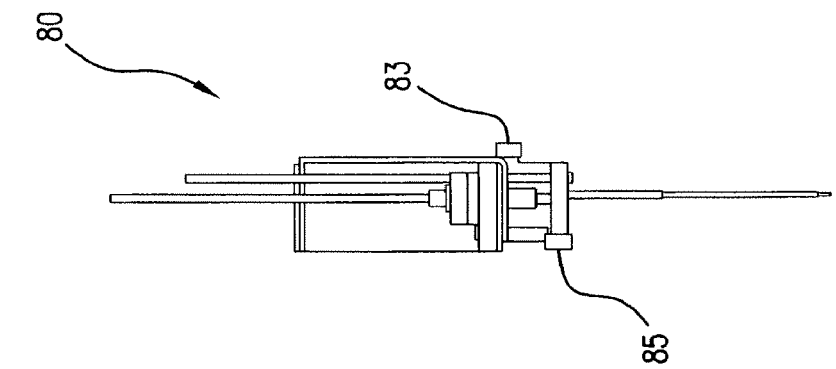
FIG. 3C is a right side view of the exemplary robotic aspiration and dispensing system of FIG. 3A.
Figure 3A:
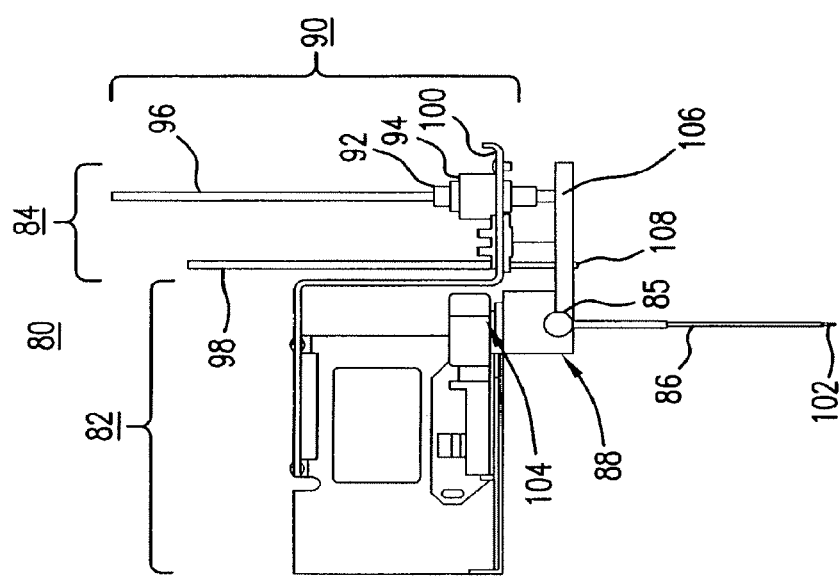
FIG. 3A is a front view of another exemplary robotic aspiration and dispensing system.
Figure 3B:
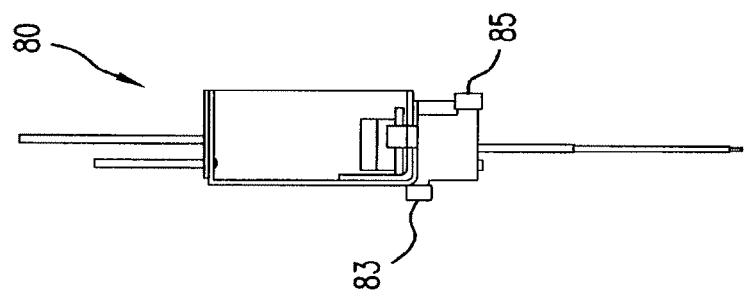
FIG. 3B is a left side view of the exemplary robotic aspiration and dispensing system of FIG. 3A.

FIG. 3A is a front view of another exemplary robotic aspiration and dispensing system 80. FIG. 3B is a left side view of the exemplary robotic aspiration and dispensing system 80 of FIG. 3A. FIG. 3C is a right side view of the exemplary robotic aspiration and dispensing system 80 of FIG. 3A.

In FIG. 3A, the exemplary robotic aspiration and dispensing system 80 has a probe mount assembly 82 on the left-hand side and a wash ring assembly 84 on the right-hand side. A probe 86 is mounted to the probe mount assembly 82.

In the exemplary embodiment, the probe 86 and the wash ring assembly 84 are able to travel horizontally and/or vertically, for example, by mechanisms similar that described above for exemplary robotic aspiration and dispensing system 2. The probe mount assembly 82 may be part of a robot such as the sample robot or the reagent robot described in U.S. Patent Publication No. 20050123445, published Jun. 9, 2005, which is hereby incorporated by reference as if fully set forth herein.

In the exemplary embodiment, the wash ring assembly 84 has a wash ring 88 and a wash ring control and guiding assembly 90. The wash ring 88 is able to move vertically up and down along the long axis of the probe 86 under control of the wash ring control and guiding assembly 90.

The wash ring control and guiding assembly 90 comprises a lead screw 92, a motor 94, a bearing 96, a guide shaft 98, and a bracket 100. The lead screw 92 and the motor 94 are fixed on the bracket 100 which can be fixed to the probe mount assembly 82 so that when the probe mount assembly 82 moves, the bracket 100 (and also the whole wash ring assembly 84) follows. Therefore, the position and movement of the wash ring 88 are controlled by both the wash ring control and guiding assembly 90 and the probe mount assembly 82.

For example, when the probe mount assembly 82 moves down, both the probe 86 and the wash ring 88 moves down along with the probe mount assembly 82. However, the wash ring 88 can also be moved toward the probe tip 102 and back to the probe head 104 by controlling of the wash ring control and guiding assembly 90. When the wash ring 88 is moved toward the position farthest away from the probe tip 102, the probe 86 can be immersed deeply into fluids such as whole blood or any other fluid.

The lead screw 92, the motor 94, and the bearing 96 are used to move and guide the wash ring 86 vertically up and down to a desired position. The bearing 96 is engaged with the lead screw 92 which is controlled by the motor 94. The motor 94 used here can be any stepping motor or linear motor. One end of the bearing 96 is fixed to through bore 106 of the wash ring 88. When the motor 94 drives, the lead screw 92 follows and screws the bearing 96 up or down depending on the direction of driving on the lead screw 92. The wash ring 88 is then moved up or down by virtue of a pull or push from the bearing 96. When the wash ring 88 moves, the probe mount assembly 82 (as well as the probe 86) can be either in a steady position or in motion relative to the ground. Therefore, the wash ring 88 can be moved relative to the probe 86 in vertical direction while the probe 7 (and also the probe mount assembly 82) can be moved relative to the ground in a vertical direction, horizontal direction or combination of the two.

The lower end of the guide shaft 98 is connected and fixed to the wash ring 88 at a bore 108. The guide shaft 98 is able to travel freely up and down, through a hole in the bracket 100, together with the wash ring 88 in order to guide and stabilize movement of the wash ring 88. This single guide shaft structure of FIG. 3A may not provide the same degree of stability as could be provided by the dual guide shafts structure previously described in connection with FIG. 1. However, this single guide shaft structure is easier to assembly and it takes less space.

The exemplary robotic aspiration and dispensing system 80 of FIG. 3A can be mounted to any robot and the movement of the exemplary robotic aspiration and dispensing system 80 is able to travel in a vertical direction, horizontal direction or combinations of horizontal directions or vertical and horizontal directions.

It will be noted that the wash ring 10 shown in FIGS. 2A-2D has the wash ring support 44 contacting the wash ring body 42 in the upper portion of the wash ring body 42. The wash ring 88 in FIGS. 3A-3C is configured such that the wash ring support contacts the wash ring body in the lower portion of the wash ring body.

In FIGS. 3A-3C, the inlet 83, or liquid port, is located at the upper portion of the wash ring 88 while the outlet 85, or vacuum port, is located at the lower portion of the wash ring 88. The dimensions of the inlet 83, the outlet 85, and the bore through which the probe passes in FIGS. 3A-3C can be the same as their corresponding parts in FIG. 1 and FIGS. 2A-2D, as discussed above.

FIG. 4A is a front view of another exemplary robotic aspiration and dispensing system 110. FIG. 4B is a left side view of the exemplary robotic aspiration and dispensing system 110 of FIG. 4A. FIG. 4C is a right side view of the exemplary robotic aspiration and dispensing system 110 of FIG. 4A.

A difference between FIG. 4A and FIG. 1 is that in FIG. 4A a bearing assembly 112 rather than guide shafts are used to provide a more stable movement of the wash ring 114. In the exemplary embodiment, the bearing assembly 112 consists of a single track rail 116 and a sled 118 movable on the rail 116. The single track rail 116 is laid out at a constant distance away from the probe 120 and in the same direction as the axis of the probe 120. The wash ring 114 has a mounting piece 122 so that the wash ring 114 can be mounted to the movable sled 118 of the bearing assembly 112. The bearing assembly 112 together with a motor 124, a lead screw 126, and a bearing 128 constitute a wash ring control and guiding assembly 130. In this way, when the wash ring 114 travels up and down, the bearing assembly 112 would guide the wash ring 114 in a stable vertical movement without much lateral vibration. Bearing 128 is connected and fixed to the wash ring 114 at bore 123. In FIGS. 4A-4C the lower portion of bearing 128 that attaches to the wash ring 114 at bore 123 is not shown in order to allow a better view of the wash ring 114.

Figure 5A:
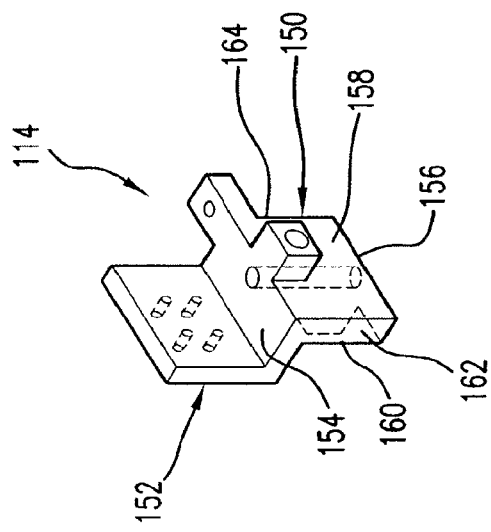
FIG. 5A is a perspective view of an exemplary wash ring used in the exemplary robotic aspiration and dispensing system of FIG. 4A.
Figure 5B:
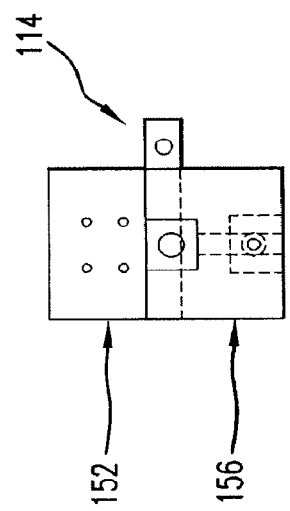
FIG. 5B is a front view of the exemplary wash ring of FIG. 5A.
Figure 5C:
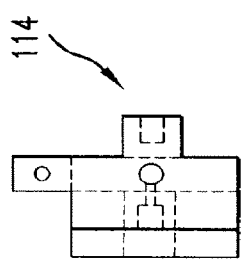
FIG. 5C is a top view of the exemplary wash ring of FIG. 5A.
Figure 5D:
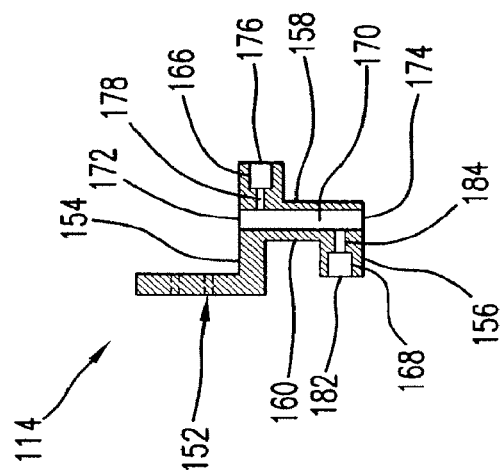
FIG. 5D is a side view of the exemplary wash ring of FIG. 5A.

FIG. 5A is a perspective view of an exemplary wash ring 114 used in the exemplary robotic aspiration and dispensing system 110 of FIG. 4A. FIG. 5B is a front view of the exemplary wash ring 114 of FIG. 5A. FIG. 5C is a top view of the exemplary wash ring 114 of FIG. 5A. FIG. 5D is a side view of the exemplary wash ring 114 of FIG. 5A.

In this embodiment, the exemplary wash ring 114 is mounted to the movable sled 118 of the bearing assembly 112, and the shape of the wash ring 114 in FIG. 5A is different from that shown in FIG. 2A. The wash ring 114 in FIG. 5A has a rectangular wash ring body 150 and a L-shaped mounting piece 152. The rectangular wash ring body 150 has a top surface 154, a bottom surface 156, front and rear walls 158, 160, respectively, two side walls 162, 164, an inlet 166, an outlet 168, and a bore 170. The bore 170 has an upper port 172 opened at the top surface 154 and a lower port 174 opened at the bottom surface 156.

In the exemplary embodiment, the inlet 166 is located at the upper portion of the wash ring body 150 with a larger end 176 opened and extended to the front wall 158 to be hooked up to a tube for wash fluid supply. A smaller end 178 of the inlet 166 is opened to the upper portion of the wash ring bore 170. The outlet 168 is located at the lower portion of the wash ring body 150 with a larger end 182 opened and extended to the rear wall 160. The larger end 182 is used to be hooked up to a tube for drainage of waste liquid. A smaller end 184 of the outlet 168 is opened to the lower portion of the wash ring bore 180.

As described above for the smaller ends of the inlet and outlet of the exemplary wash ring 10, the smaller end 184 of the outlet 168 is larger than the inner diameter of the smaller end 178 of the inlet 166 in the exemplary wash ring 114. In some embodiments, the inner diameter of the smaller end 178 is about 0.25× to about 0.75× the inner diameter of the smaller end 184. In some embodiments, the inner diameter of the smaller end 178 is about 0.25× to about 0.5× the inner diameter of the smaller end 184. In certain embodiments, the inner diameter of the smaller end 178 is about 0.5× the inner diameter of the smaller end 184. The inner diameter of the smaller end 184 of the outlet 168 can, for example, be about 0.02 to about 0.8 inches, about 0.025 inches to about 0.5 inches, or about 0.03 inches to about 0.15 inches. The inner diameter of the smaller end 178 of the inlet 166 can, for example, be about 0.01 to about 0.4 inches, about 0.0125 inches to about 0.25 inches, or about 0.015 inches to about 0.075 inches.

Figure 6C:
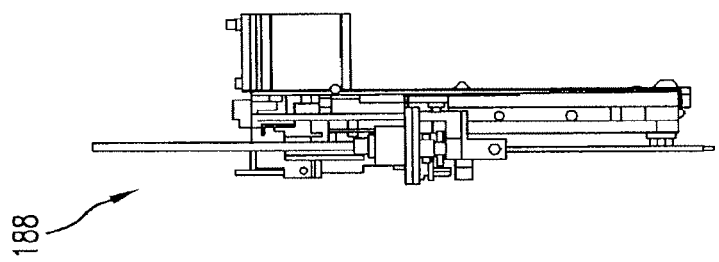
FIG. 6C is a right side view of the exemplary robotic aspiration and dispensing system of FIG. 6A.
Figure 6A:
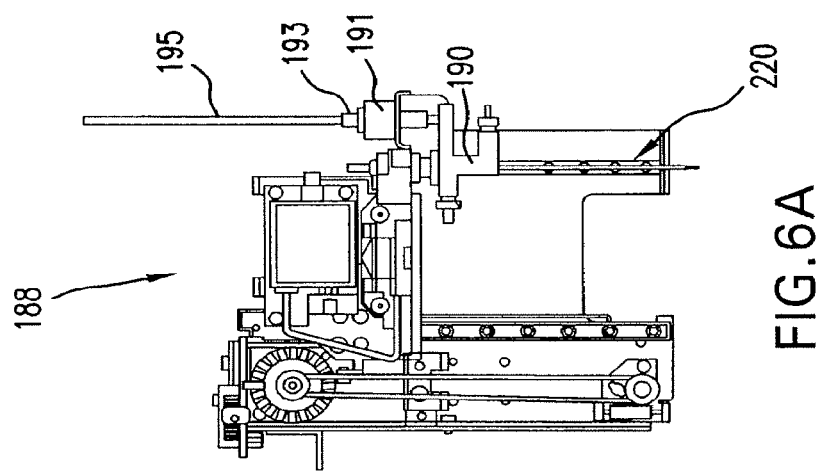
FIG. 6A is a front view of another exemplary robotic aspiration and dispensing system.
Figure 6B:
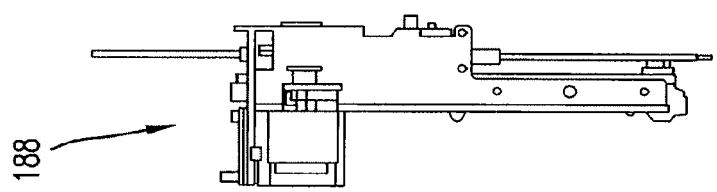
FIG. 6B is a left side view of the exemplary robotic aspiration and dispensing system of FIG. 6A.

FIG. 6A is a front view of another exemplary robotic aspiration and dispensing system 188. FIG. 6B is a left side view of the exemplary robotic aspiration and dispensing system 188 of FIG. 6A. FIG. 6C is a right side view of the exemplary robotic aspiration and dispensing system 188 of FIG. 6A. The configurations in FIG. 6A and FIG. 4A are similar except that the location setup of the inlet and the outlet of the wash ring 114 in FIG. 4A are rotated 90° compared with the wash ring 190 in FIG. 6A.

Figure 7A:
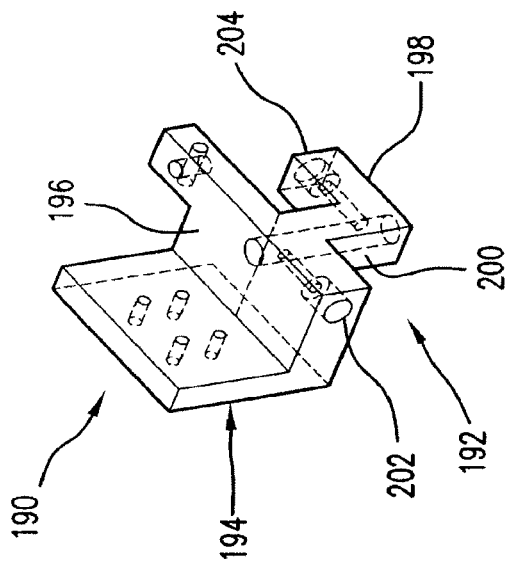
FIG. 7A is a perspective view of an exemplary wash ring used in the exemplary robotic aspiration and dispensing system of FIG. 6A.
Figure 7B:
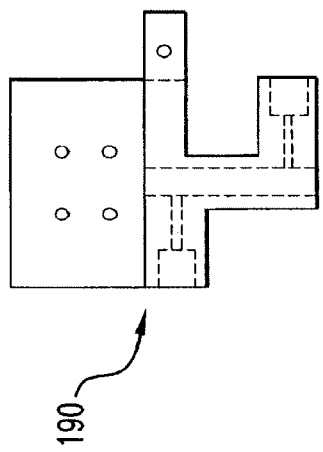
FIG. 7B is a front view of the exemplary wash ring of FIG. 7A.
Figure 7C:
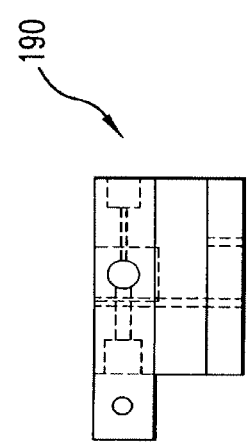
FIG. 7C is a top view of the exemplary wash ring of FIG. 7A.
Figure 7D:
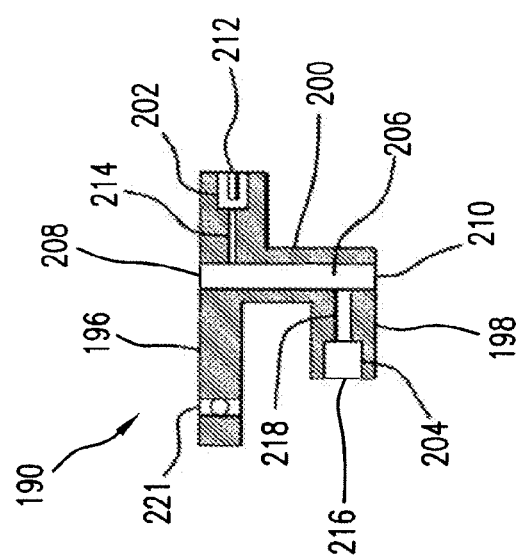
FIG. 7D is a side view of the exemplary wash ring of FIG. 7A.

FIG. 7A is a perspective view of an exemplary wash ring 190 used in the exemplary robotic aspiration and dispensing system 188 of FIG. 6A. The wash ring 190 in FIG. 7A has a J-shaped wash ring body 192 and a L-shaped mounting piece 194. The J-shaped wash ring body 192 has a top surface 196, a bottom surface 198, a vertical trunk 200, an inlet 202, an outlet 204, and a bore 206. The bore 206 has an upper port 208 opened at the top surface 196 and a lower port 210 opened at the bottom surface 198. FIG. 7B is a front view of the exemplary wash ring 190 of FIG. 7A. FIG. 7C is a top view of the exemplary wash ring 190 of FIG. 7A. FIG. 7D is a cutaway rear view of the exemplary wash ring 190 of FIG. 7A.

Figure 8C:
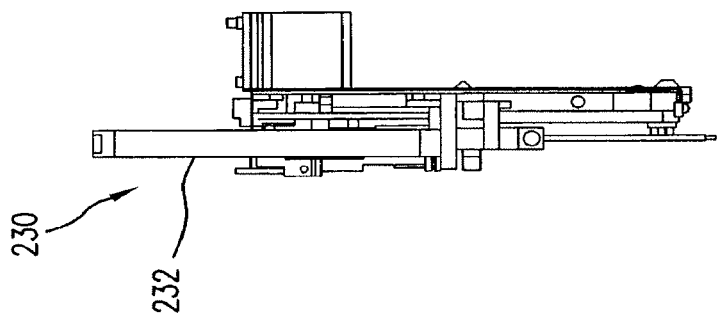
FIG. 8C is a right side view of the exemplary robotic aspiration and dispensing system of FIG. 8A.
Figure 8A:
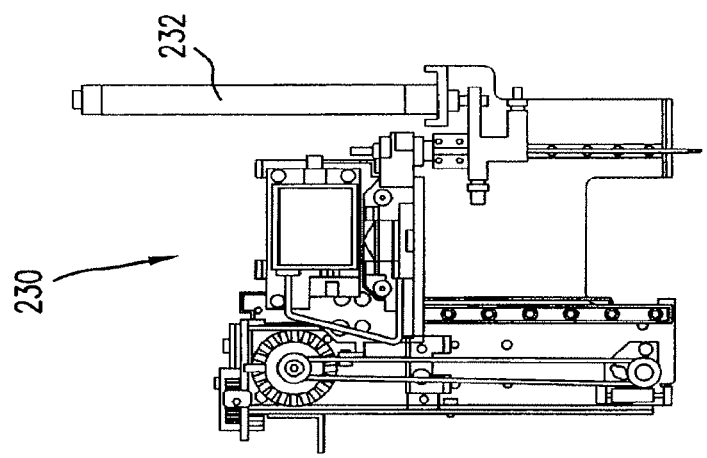
FIG. 8A is a front view of another exemplary robotic aspiration and dispensing system.

In various embodiments, wash ring 190 can be mounted using bore 221 to a bearing, for example, the bearing 195 as shown in FIG. 6A, or to an air cylinder, for example, the air cylinder 232 as shown in FIG. 8A, as discussed below.

In the exemplary embodiment, the inlet 202 has a larger end 212 opened and extended to the upper portion of the vertical trunk 200. The inlet can be hooked up to a tube for wash fluid supply. A smaller end 214 of the inlet 202 is opened to the upper portion of the wash ring bore 206. The outlet 204 has a larger end 216 opened and extended to the lower portion of the trunk 200. The outlet 204 and the inlet 202 are located at the opposite side of the trunk 200. The larger end 216 can be hooked up to a tube for drainage of waste liquid. A smaller end 218 of the outlet 204 is opened to the lower portion of the wash ring bore 200.

As described above for the smaller ends of the inlets and outlets of the exemplary wash ring 10 and the exemplary wash ring 114 described above, the inner diameter of the smaller end 218 of the outlet 204 is larger than the inner diameter of the smaller end 214 of the inlet 202 in the exemplary wash ring 190. The size relationships between smaller end 214 to smaller end 218 and the ranges of the inner diameters of smaller end 214 and smaller end 218 can, for example, be as described above with respect to smaller ends of the inlets and outlets of the exemplary wash ring 10 or the exemplary wash ring 114.

In certain embodiments, ratio of the inner diameter of the outlet port opening into the bore of the wash ring to the inner diameter of the inlet port opening into the bore of the wash ring is about 4 to 1, about 3 to 1 or about 2 to 1.

One advantage of exemplary wash ring 190 is that it requires less material and can have less mass. Moreover, most of its mass is close to the wash ring bore 206 so that it has a relatively small moment of inertia. Therefore, when the wash ring 190 is moved in a vertical direction along the guide rail 220, its movement is stable and causes less vibration.

Figure 8B:
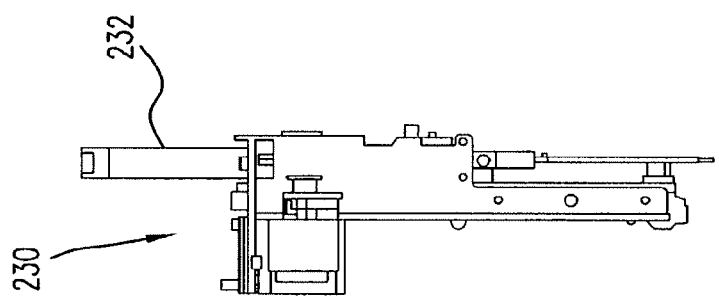
FIG. 8B is a left side view of the exemplary robotic aspiration and dispensing system of FIG. 8A.

FIG. 8A is a front view of another exemplary robotic aspiration and dispensing system 230. FIG. 8B is a left side view of the exemplary robotic aspiration and dispensing system 230 of FIG. 8A. FIG. 8C is a right side view of the exemplary robotic aspiration and dispensing system 230 of FIG. 8A. The configurations in FIG. 8A and FIG. 6A are similar except that in FIG. 8A, an air cylinder 232 is used to replace the motor 191, the lead screw 193, and the bearing 195 in FIG. 6A. The air cylinder 232 can be of any pneumatic cylinder known to a person skilled in the art.

The exemplary wash ring 190 as represented in FIGS. 7A-7D can, for example, is used in the exemplary robotic aspiration and dispensing system 230 shown in FIG. 8A.

Many modifications to the preferred embodiment described above are possible without departing from the inventive features of this device. Accordingly, this patent is not limited to the preferred embodiment set forth above, but is of the full scope and breadth of the following claims.

It is claimed:

1. A method for cleaning a probe in a robotic aspiration and dispensing system as the probe is in motion, aspirating and/or dispensing, the method comprising:
   providing a robotic aspiration and dispensing system comprising a probe and a wash ring, the wash ring comprising:
   a top surface,
   a bottom surface,
   an outer side surface,
   an inner surface forming a bore comprising an inner diameter, a long axis, an upper portion with an opening in the top surface and a lower portion with an opening in the bottom surface,
   an inlet comprising an opening in the top surface, bottom surface or outer side surface and an opening in the upper bore portion; and
   an outlet comprising an opening in the top surface, bottom surface or outer side surface and an opening in the lower bore portion,
   wherein the inner diameter of the bore is adapted to receive the probe such that when the probe is present in the bore, a space is formed between the exterior surface of the probe and the inner surface forming the bore, wherein the width of the space between the exterior surface of the probe and inner surface forming the bore is about 0.008 inches to about 0.12 inches,
   wherein the diameter of the outlet opening in the lower bore portion is larger than the diameter of the inlet opening in the upper bore portion, and wherein the bore is cylindrical between the inlet opening in the upper bore portion and outlet opening in the lower bore portion;
   wherein a portion of the probe to be washed is present in the bore forming the space between the probe and the inner surface of the bore,
   adding fluid into the bore of the wash ring through the inlet;
   removing fluid by suction from the bore of the wash ring through the outlet;
   wherein the adding fluid and removing fluid steps can be performed as the probe is in motion, aspirating and/or dispensing.

2. The method according to claim 1 further comprising the following step:
   guiding the vertical movement of the wash ring with a guide shaft along a longitudinal axis of the probe.

3. The method according to claim 1, wherein the inner surface of the bore is made of a hydrophobic material or coated with a hydrophobic material.

4. The method according to claim 3, wherein the hydrophobic material is plastic, silicon, polyethylene, or TEFLON.

5. The method according to claim 1, wherein the width of the space formed between the exterior surface of the probe and the inner surface forming the bore is about 0.01 inches to about 0.12 inches.

6. The method according to claim 1, wherein the inlet opening in the inner surface forming the bore and the outlet opening in the inner surface forming the bore are on opposing sides of the bore.

7. The method according to claim 1, wherein the ratio of the diameter of the outlet opening in the inner surface forming the bore to the diameter of the inlet opening in the inner surface forming the bore is about 2 to 1 or about 3 to 1.

* * * * *